United States Patent
Scheller et al.

(10) Patent No.: US 9,572,714 B2
(45) Date of Patent: *Feb. 21, 2017

(54) STEERABLE LASER PROBE

(71) Applicant: Katalyst Surgical, LLC, Chesterfield, MO (US)

(72) Inventors: Gregg D Scheller, Wildwood, MO (US); Craig Moore, O'Fallon, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,432

(22) Filed: Jul. 9, 2015

(65) Prior Publication Data

US 2015/0335476 A1    Nov. 26, 2015

Related U.S. Application Data

(63) Continuation of application No. 13/602,037, filed on Aug. 31, 2012, now Pat. No. 9,113,995.

(51) Int. Cl.
| | | |
|---|---|---|
| *A61B 18/18* | (2006.01) | |
| *A61F 9/008* | (2006.01) | |
| *A61F 2/30* | (2006.01) | |
| *A61B 18/00* | (2006.01) | |
| *A61B 18/22* | (2006.01) | |

(52) U.S. Cl.
CPC .......... *A61F 9/008* (2013.01); *A61F 9/00802* (2013.01); *A61F 9/00823* (2013.01); *A61B 2018/0091* (2013.01); *A61B 2018/00196* (2013.01); *A61B 2018/00202* (2013.01); *A61B 2018/00589* (2013.01); *A61B 2018/225* (2013.01); *A61B 2018/2238* (2013.01); *A61F 2002/3037* (2013.01); *A61F 2009/00863* (2013.01)

(58) Field of Classification Search
CPC ... A61F 9/008; A61F 9/00802; A61F 9/00823
USPC .......................................................... 606/4
See application file for complete search history.

(56) References Cited

U.S. PATENT DOCUMENTS

| | | | |
|---|---|---|---|
| 5,190,050 | A | 3/1993 | Nitzsche |
| 5,355,871 | A | 10/1994 | Hurley et al. |

(Continued)

FOREIGN PATENT DOCUMENTS

| | | |
|---|---|---|
| EP | 0900547 B1 | 3/1999 |
| NL | WO 2013/133717 | 9/2013 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle, and inner bore of the handle, an actuation lever of the handle, a housing tube, and an optic fiber disposed within the inner bore of the handle and the housing tube. The housing tube may have a first housing tube portion having a first stiffness and a second housing tube portion having a second stiffness. The second stiffness may be greater than the first stiffness.

20 Claims, 15 Drawing Sheets

(56) References Cited

U.S. PATENT DOCUMENTS

| | | |
|---|---|---|
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 6,123,699 A | 9/2000 | Webster, Jr. |
| 6,126,654 A | 10/2000 | Giba et al. |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | Mc Gowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0272975 A1 | 12/2005 | McWeeney et al. |
| 2005/0277874 A1* | 12/2005 | Selkee ............... A61M 25/0147 604/95.04 |
| 2007/0185514 A1 | 8/2007 | Kirchhevel |
| 2009/0018993 A1 | 1/2009 | Dick et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |

* cited by examiner

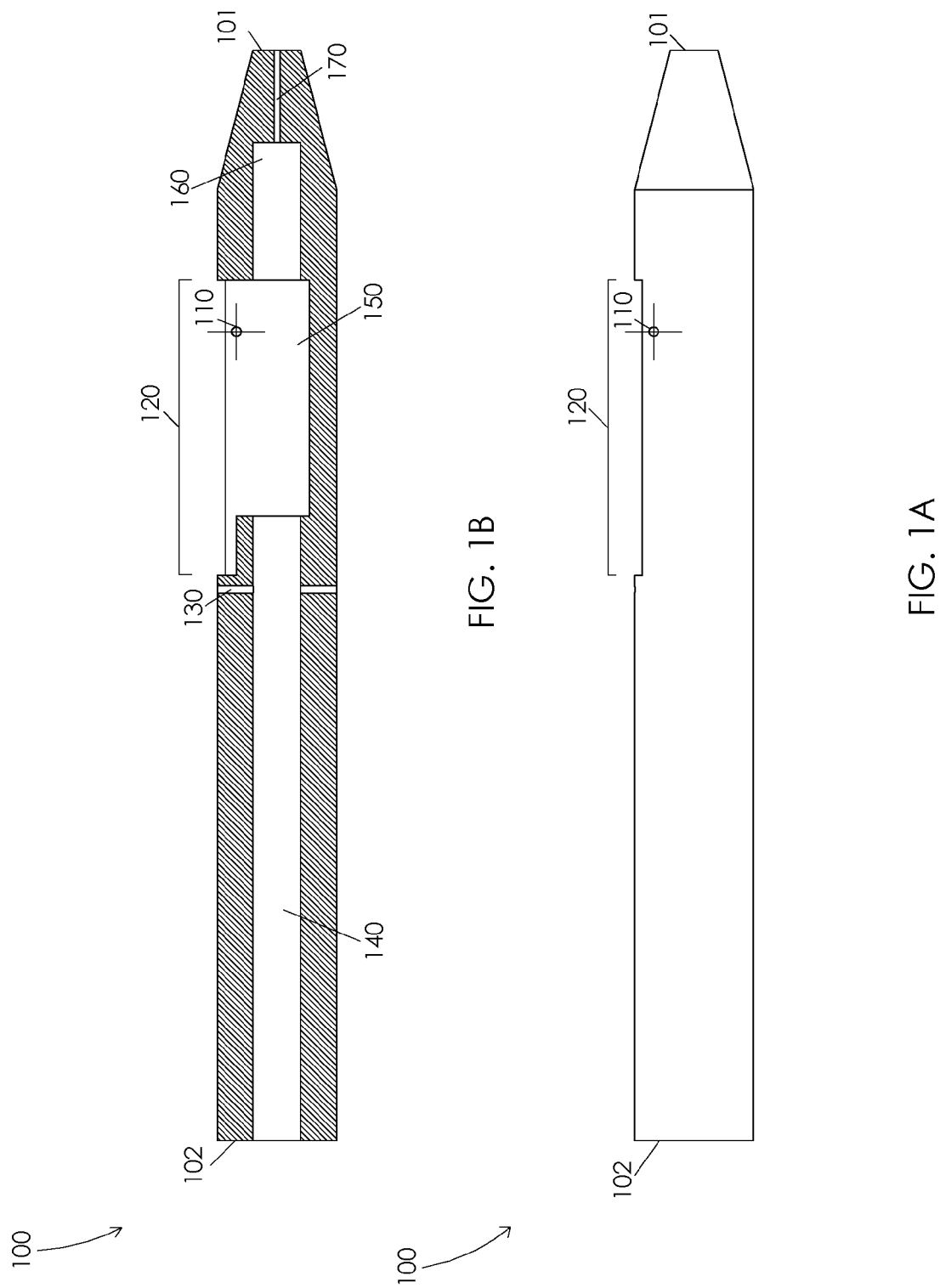

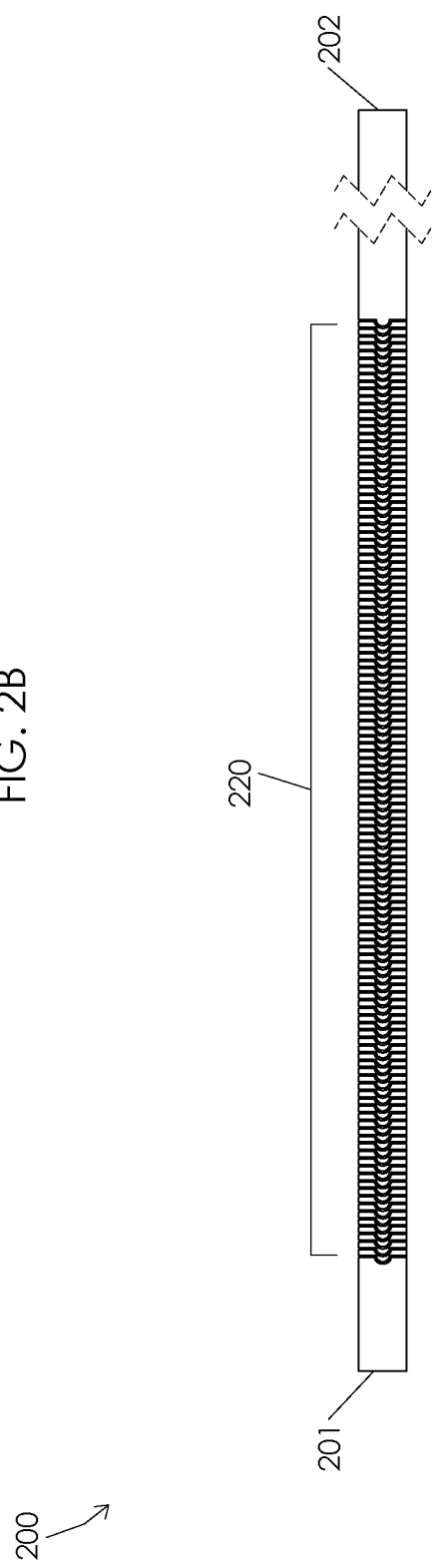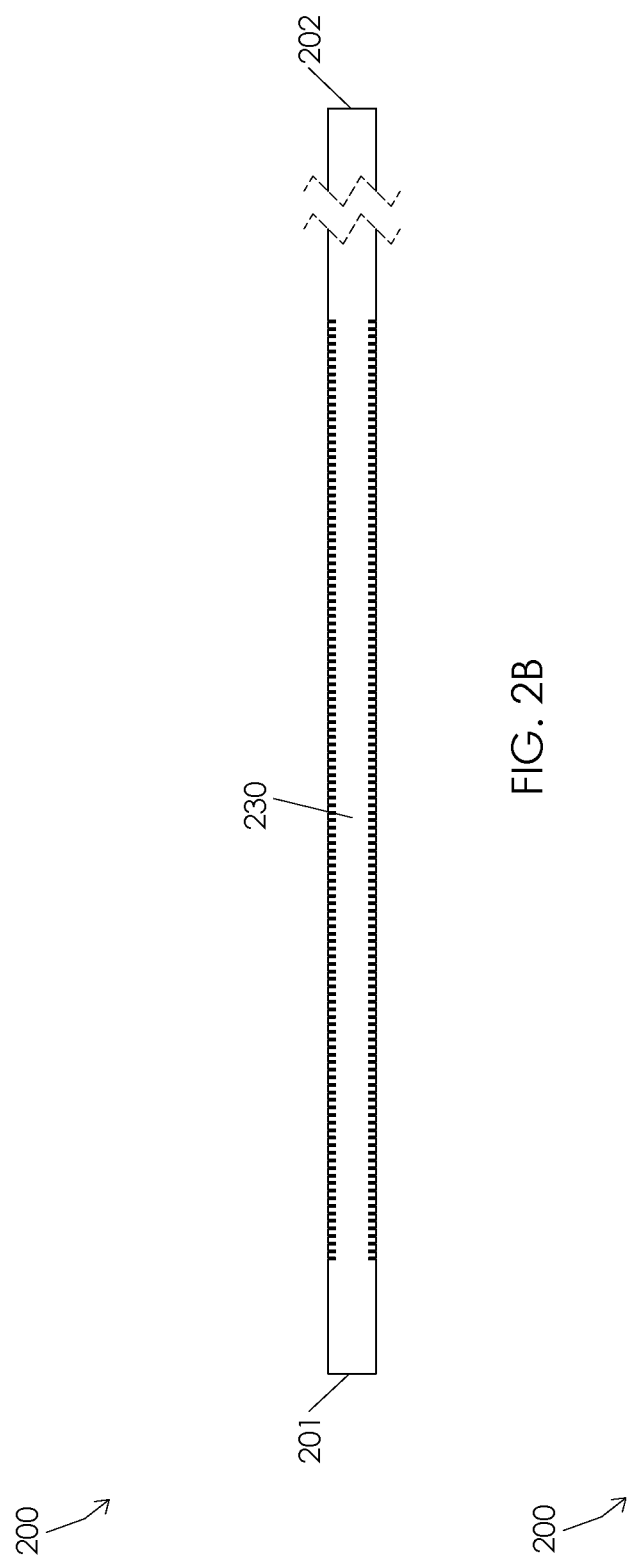

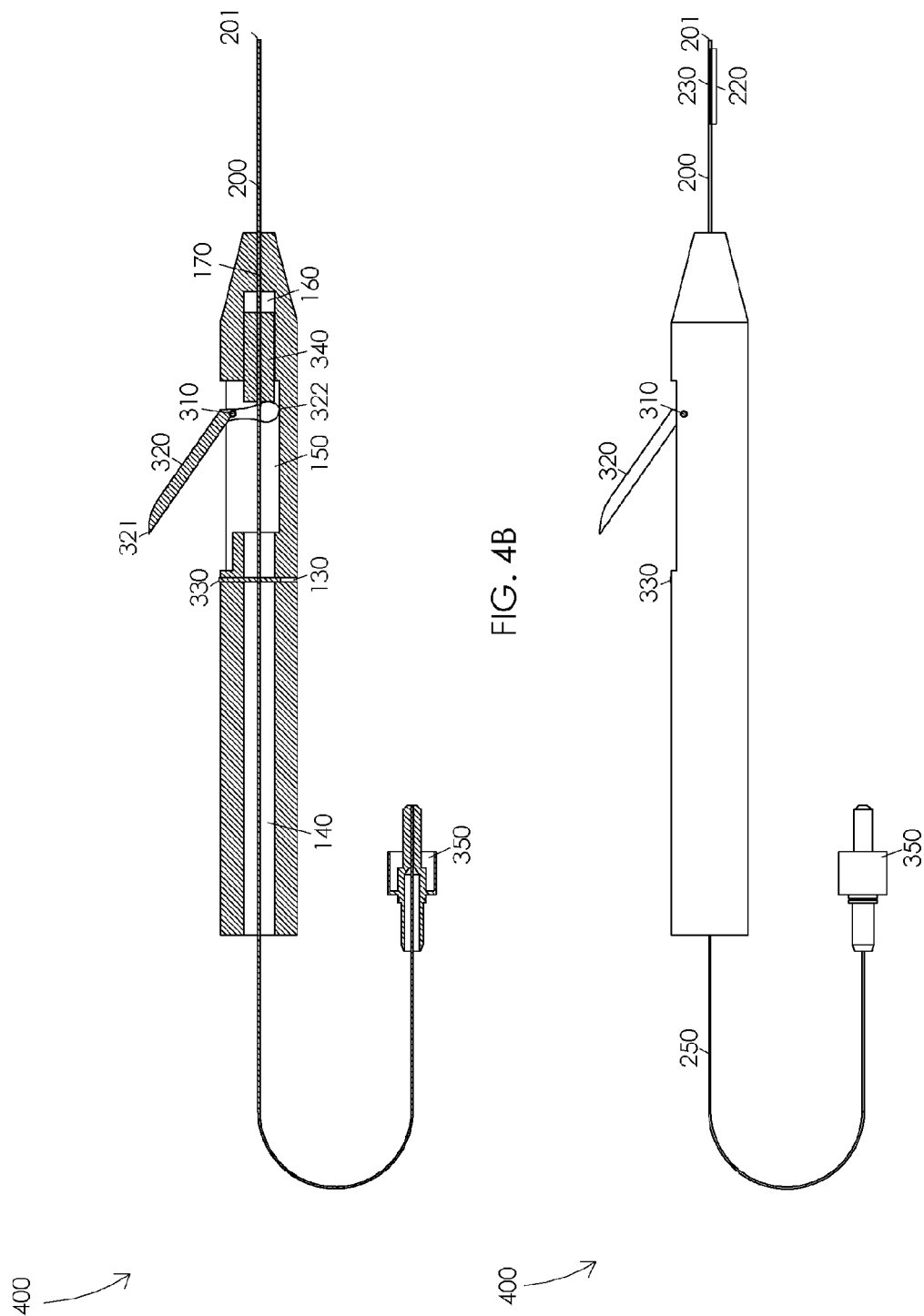

STEERABLE LASER PROBE

CROSS-REFERENCE TO RELATED APPLICATIONS

This Application is a continuation of prior application Ser. No. 13/602,037, filed Aug. 31, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, and inner bore of the handle, an actuation lever of the handle, a housing tube, and an optic fiber disposed within the inner bore of the handle and the housing tube. Illustratively, the housing tube may comprise a first housing tube portion having a first stiffness and a second housing tube portion having a second stiffness. In one or more embodiments, the second stiffness may be greater than the first stiffness.

Illustratively, an actuation of the actuation lever may be configured to gradually curve the housing tube. In one or more embodiments, a gradual curving of the housing tube may be configured to gradually curve the optic fiber. Illustratively, an actuation of the actuation lever may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 2A, 2B, and 2C are schematic diagrams illustrating a housing tube;

FIGS. 4A and 4B are schematic diagrams illustrating an assembled steerable laser probe;

DETAILED DESCRIPTION OF AN ILLUSTRATIVE EMBODIMENT

Figure 2C:
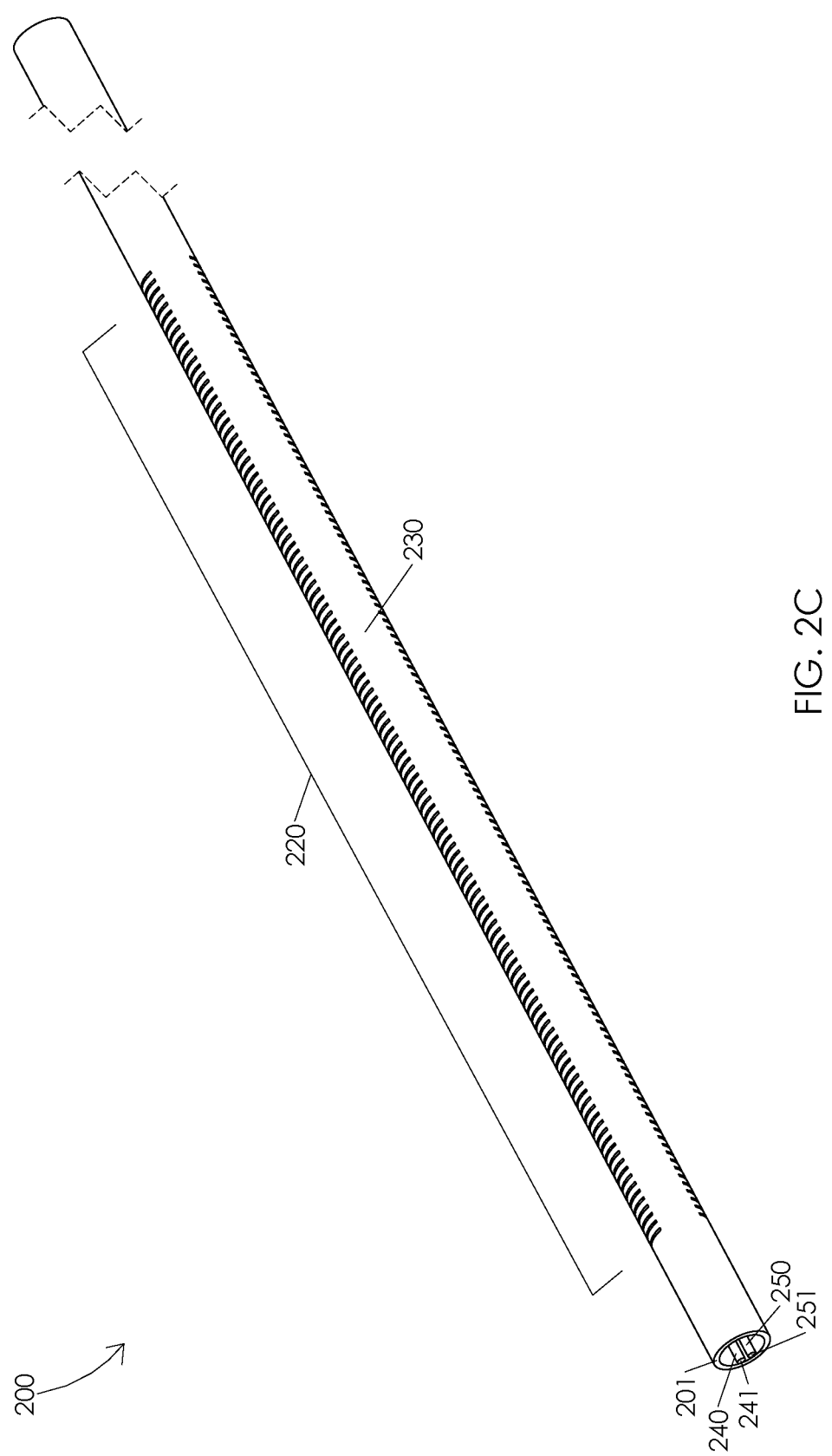

FIGS. 1A and 1B are schematic diagrams illustrating a handle 100. FIG. 1A illustrates a side view of handle 100. In one or more embodiments, handle 100 may comprise a handle distal end 101, a handle proximal end 102, a pivot pin housing 110, and an actuation lever channel 120. FIG. 1B illustrates a cross-sectional view of handle 100. In one or more embodiments, handle 100 may comprise a fixation pin housing 130, an inner bore 140, an actuation lever guide 150, a piston guide 160, and a housing tube guide 170. Handle 100 may be manufactured from any suitable material, e.g., polymers, metals, metal alloys, etc., or from any combination of suitable materials.

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. Illustratively, housing tube 200 may be manufactured with dimensions suitable for performing microsurgical procedures, e.g., ophthalmic surgical procedures.

FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, housing tube 200 may comprise a non-uniform inner diameter or a non-uniform outer diameter, e.g., to vary a stiffness of one or more portions of housing tube 200. Illustratively, a first housing tube portion 220 may comprise a first inner diameter of housing tube 200 and a second housing tube portion 230 may comprise a second inner diameter of housing tube 200. In one or more embodiments, the first inner diameter of housing tube 200 may be larger than the second inner diameter of housing tube 200. Illustratively, a first housing tube portion 220 may comprise a first outer diameter of housing tube 200 and a second housing tube portion 230 may comprise a second outer diameter of housing tube 200. In one or more embodiments, the first outer diameter of housing tube 200 may be smaller than the second outer diameter of housing tube 200.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 250 may be disposed within housing tube 200. In one or more embodiments, optic fiber 250 may be disposed within housing tube 200 wherein an optic fiber distal end 251 is adjacent to housing tube distal end 201. Illustratively, optic fiber 250 may be disposed within housing tube 200 wherein optic fiber 250 may be adjacent to a portion of first housing tube portion 220. In one or more embodiments, a portion of optic fiber 250 may be fixed to an inner portion of housing tube 200, e.g., by an adhesive or by any suitable fixation means.

Illustratively, a cable 240 may be disposed within housing tube 200. In one or more embodiments, cable 240 may be disposed within housing tube 200 wherein a cable distal end 241 may be adjacent to housing tube distal end 201. Illustratively, cable 240 may be disposed within housing tube 200 wherein cable 240 may be adjacent to a portion of first housing tube portion 220. In one or more embodiments, a portion of cable 240 may be fixed to an inner portion of housing tube 200, e.g., by an adhesive or by any suitable fixation means.

Figure 3:
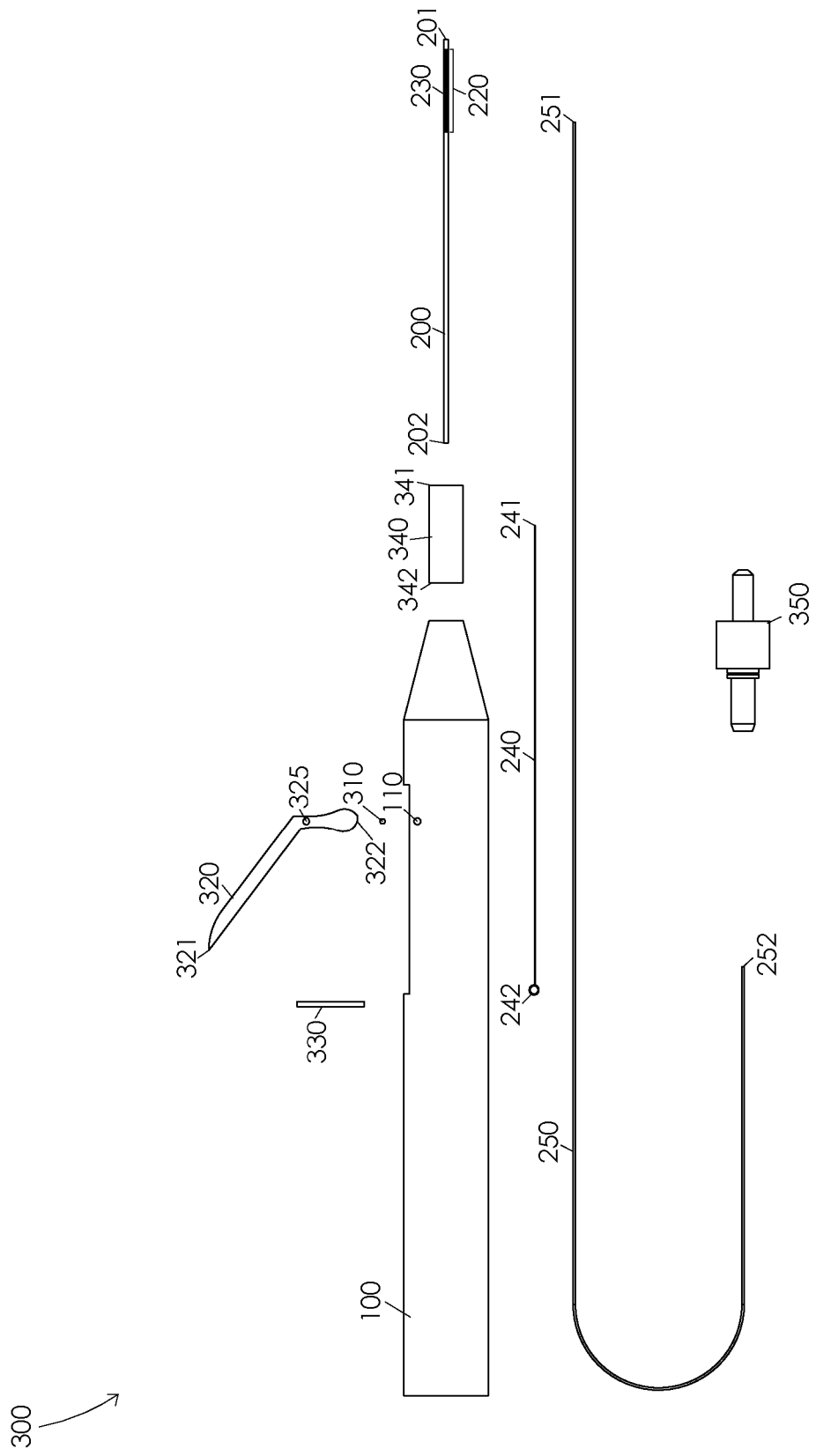
FIG. 3 is a schematic diagram illustrating a steerable laser probe assembly.

FIG. 3 is a schematic diagram illustrating a steerable laser probe assembly 300. In one or more embodiments, steerable laser probe assembly 300 may comprise a handle 100, a pivot pin 310, an actuation lever 320 having an actuation lever distal end 321 and an actuation lever proximal end 322, a fixation pin 330, a piston 340 having a piston distal end 341 and a piston proximal end 342, a housing tube 200 having a housing tube distal end 201 and a housing tube proximal end 202, a cable 240 having a cable distal end 241 and a cable proximal loop 242, an optic fiber 250 having an optic fiber distal end 251 and an optic fiber proximal end 252, and a light source interface 350. Illustratively, light source interface 350 may be configured to interface with optic fiber 250, e.g., at optic fiber proximal end 252. In one or more embodiments, light source interface 350 may comprise a standard light source connecter, e.g., an SMA connector.

FIGS. 4A and 4B are schematic diagrams illustrating an assembled steerable laser probe 400. FIG. 4A illustrates a side view of an assembled steerable laser probe 400. FIG. 4B illustrates a cross-sectional view of an assembled steerable laser probe 400. Illustratively, piston 340 may be disposed within piston guide 160. In one or more embodiments, piston 340 may be configured to actuate within piston guide 160. Illustratively, a portion of housing tube 200 may be fixed to piston 340, e.g., housing tube proximal end 202 may be fixed to piston distal end 341. In one or more embodiments, a portion of housing tube 200 may be fixed to piston 340, e.g., by an adhesive or any suitable fixation means. Illustratively, a portion of housing tube 200 may be disposed within piston 340, e.g., housing tube proximal end 202 may be disposed within piston 340. In one or more embodiments, a portion of housing tube 200 may be fixed within piston 340, e.g., by an adhesive or by any suitable means. Illustratively, a portion of housing tube 200 may be disposed within housing tube guide 170. In one or more embodiments, housing tube 200 may be configured to actuate within housing tube guide 170.

Illustratively, a portion of actuation lever 320 may be disposed within actuation lever guide 150, e.g., actuation lever proximal end 322 may be disposed within actuation lever guide 150. In one or more embodiments, actuation lever 320 may comprise a pivot pin chamber 325 configured to enclose a portion of pivot pin 310. Illustratively, pivot pin 310 may be disposed within both pivot pin housing 110 and pivot pin chamber 325. In one or more embodiments, pivot pin 310 may be fixed within pivot pin housing 110. Illustratively, pivot pin 310 may be fixed within pivot pin housing 110, e.g., by an adhesive or by any suitable fixation means. In one or more embodiments, pivot pin 310 may be configured to fix a portion of actuation lever 320 to handle 100, e.g., at pivot pin chamber 325. Illustratively, when pivot pin 310 is disposed within pivot pin chamber 325, pivot pin 310 may be configured to limit an actuation of actuation lever 320, e.g., to allow rotational actuation of actuation lever 320 about pivot pin 310. In one or more embodiments, actuation lever 320 may be configured to rotate about pivot pin 310, e.g., in response to an application of a force to a portion of actuation lever 320. Illustratively, pivot pin chamber 325 may be coated by a lubricant, e.g., Teflon, configured to facilitate a rotation of actuation lever 320 about pivot pin 310.

In one or more embodiments, optic fiber 250 may be disposed within inner bore 140, actuation lever guide 150, piston guide 160, piston 340, housing tube guide 170, and housing tube 200. Illustratively, optic fiber 250 may be disposed within housing tube 200 wherein optic fiber distal end 251 may be adjacent to housing tube distal end 201. In one or more embodiments, a portion of optic fiber 250 may be fixed to an inner portion of housing tube 200. Illustratively, a portion of optic fiber 250 may be fixed within housing tube 200, e.g., by an adhesive or any suitable fixation means.

In one or more embodiments, cable 240 may be disposed within fixation pin housing 130, inner bore 140, actuation lever guide 150, piston guide 160, piston 340, housing tube guide 170, and housing tube 200. Illustratively, cable 240 may be disposed within housing tube 200 wherein cable distal end 241 may be adjacent to housing tube distal end 201. In one or more embodiments, cable 240 may be disposed within housing tube 200 wherein a portion of cable 240 may be adjacent to first housing tube portion 220. Illustratively, a portion of cable 240 may be fixed to an inner portion of housing tube 200. In one or more embodiments, a portion of cable 240 may be fixed within housing tube 200, e.g., by an adhesive or any suitable fixation means. Illustratively, fixation pin 330 may be configured to fix cable 240 in a position relative to handle 100. In one or more embodiments, fixation pin 330 may be disposed within fixation pin housing 130 and cable proximal loop 242. Illustratively, fixation pin 330 may comprise a set screw configured to firmly fix cable 240 in a position relative to handle 100. In one or more embodiments, a portion of cable 240 may be fixed to fixation pin 330, e.g., by an adhesive or any suitable fixation means.

Illustratively, an actuation of actuation lever 320 about pivot pin 310 in a counter-clockwise direction may be configured to cause actuation lever 320 to apply a force to piston proximal end 342. In one or more embodiments, an application of a force to piston proximal end 342 may be configured to actuate piston 340 within piston guide 160. Illustratively, an application of a force to piston proximal end 342 may be configured to extend piston 340 relative to handle proximal end 102. In one or more embodiments, an extension of piston 340 relative to handle proximal end 102 may be configured to extend housing tube 200 relative to handle proximal end 102. Illustratively, an extension of housing tube 200 relative to handle proximal end 102 may be configured to extend housing tube 200 relative to cable 240. In one or more embodiments, an extension of housing tube 200 relative to cable 240 may be configured to cause cable 240 to apply a force, e.g., a compressive force, to a portion of housing tube 200. For example, if a portion of cable 240 is fixed in a position relative to handle 100 and a portion of cable 240 is also fixed within housing tube 200, then an extension of housing tube 200 relative to handle 100 and cable 240 may apply a force to a portion of housing tube 200. Illustratively, an application of a force to a portion of housing tube 200 may be configured to compress a portion of housing tube 200, e.g., first housing tube portion 220, causing housing tube 200 to gradually curve. In one or more embodiments, a gradual curving of housing tube 200 may be configured to gradually curve optic fiber 250.

Illustratively, an actuation of actuation lever 320 about pivot pin 310 in a clockwise direction may be configured to cause actuation lever 320 to reduce a force applied to piston proximal end 342. In one or more embodiments, a reduction of a force applied to piston proximal end 342 may be configured to actuate piston 340 within piston guide 160. Illustratively, a reduction of a force applied to piston proximal end 342 may be configured to retract piston 340 relative to handle proximal end 102. In one or more embodiments, a retraction of piston 340 relative to handle proximal end 102 may be configured to retract housing tube 200 relative to handle proximal end 102. Illustratively, a retraction of housing tube 200 relative to handle proximal end 102 may be configured to retract housing tube 200 relative to cable 240. In one or more embodiments, a retraction of housing tube 200 relative to cable 240 may be configured to cause cable 240 to reduce a force, e.g., a compressive force, applied to a portion of housing tube 200. Illustratively, a reduction of a force applied to a portion of housing tube 200 may be configured to decompress a portion of housing tube 200, e.g., first housing tube portion 220, causing housing tube 200 to gradually straighten. In one or more embodiments, a gradual straightening of housing tube 200 may be configured to gradually straighten optic fiber 250.

Figure 5A:
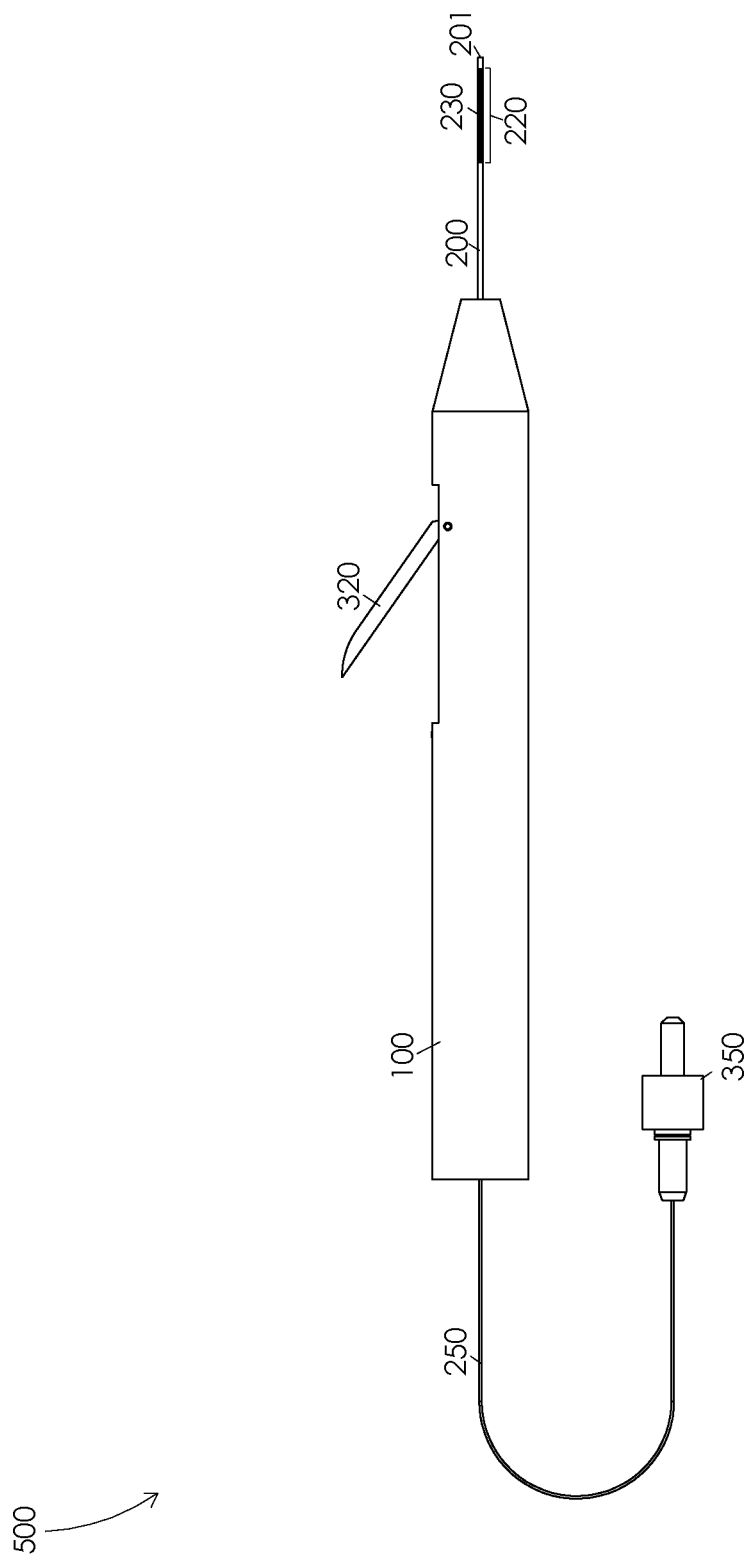
FIGS. 5A, 5B, 5C, 5D, and 5E are schematic diagrams illustrating a gradual curving of an optic fiber.

FIGS. 5A, 5B, 5C, 5D, and 5E are schematic diagrams illustrating a gradual curving of an optic fiber 250. FIG. 5A illustrates a straight optic fiber 500. In one or more embodiments, optic fiber 250 may comprise a straight optic fiber 500, e.g., when piston 340 is fully retracted relative to handle proximal end 102. Illustratively, optic fiber 250 may comprise a straight optic fiber 500, e.g., when housing tube 200 is fully refracted relative to cable 240. In one or more embodiments, optic fiber 250 may comprise a straight optic fiber 500, e.g., when first housing tube portion 220 is fully decompressed. Illustratively, a line tangent to optic fiber distal end 251 may be parallel to a line tangent to housing tube proximal end 202, e.g., when optic fiber 250 comprises a straight optic fiber 500.

Figure 5B:
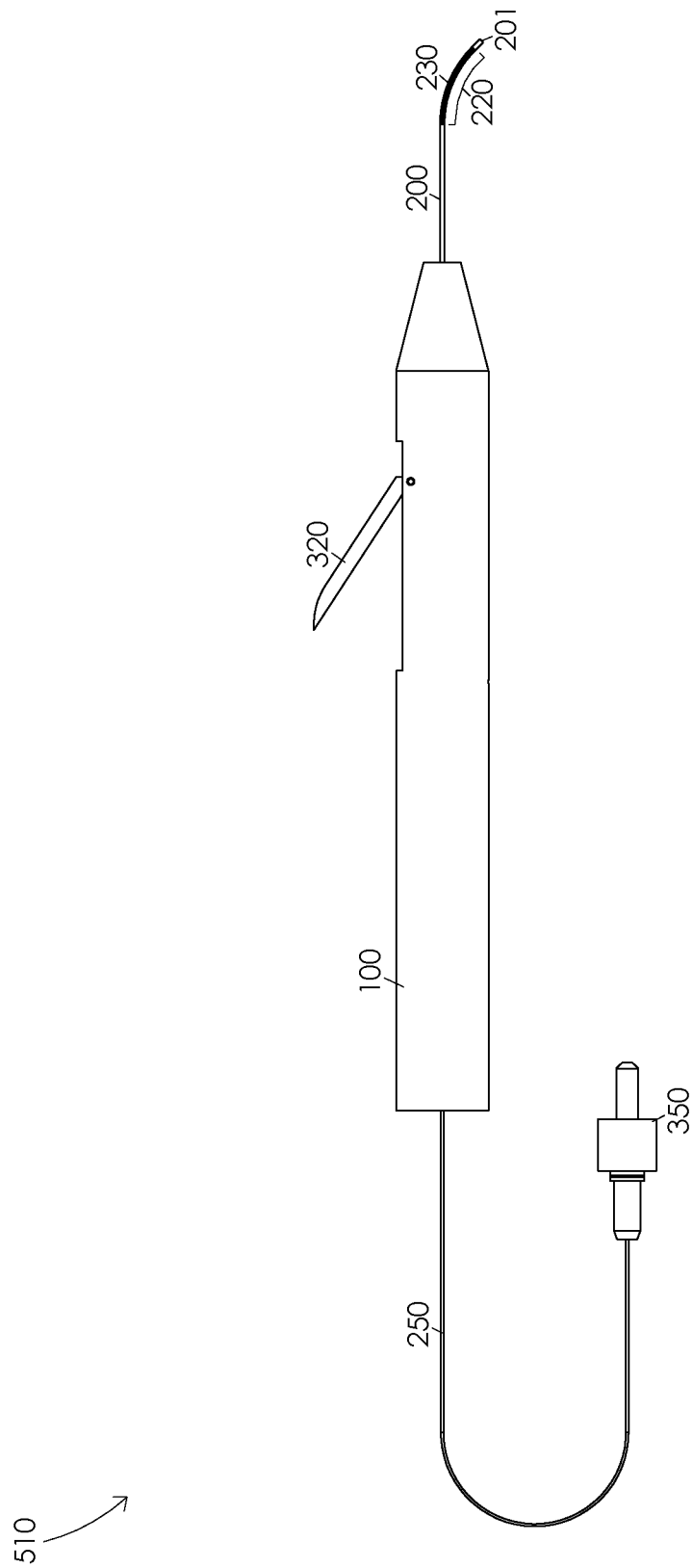

FIG. 5B illustrates an optic fiber in a first curved position 510. In one or more embodiments, a rotation of actuation lever 320 about pivot pin 310 in a counter-clockwise direction may be configured to gradually curve optic fiber 250 from a straight optic fiber 500 to an optic fiber in a first curved position 510. Illustratively, a rotation of actuation lever 320 about pivot pin 310 in a counter-clockwise direction may be configured to gradually extend piston 340 relative to handle proximal end 102. In one or more embodiments, a gradual extension of piston 340 relative to handle proximal end 102 may be configured to gradually extend housing tube 200 relative to cable 240. Illustratively, a gradual extension of housing tube 200 relative to cable 240 may be configured to cause cable 240 to apply a force, e.g., a compressive force, to a portion of housing tube 200. In one or more embodiments, an application of a force to a portion of housing tube 200 may be configured to compress a portion of housing tube 200, e.g., first housing tube portion 220. Illustratively, a compression of a portion of housing tube 200, e.g., first housing tube portion 220, may be configured to gradually curve housing tube 200. In one or more embodiments, a gradual curving of housing tube 200 may be configured to gradually curve optic fiber 250, e.g., from a straight optic fiber 500 to an optic fiber in a first curved position 510. Illustratively, a line tangent to optic fiber distal end 251 may intersect a line tangent to housing tube proximal end 202 at a first angle, e.g., when optic fiber 250 comprises an optic fiber in a first curved position 510. In one or more embodiments, the first angle may comprise any angle greater than zero degrees. For example, the first angle may comprise a 45 degree angle.

Figure 5C:
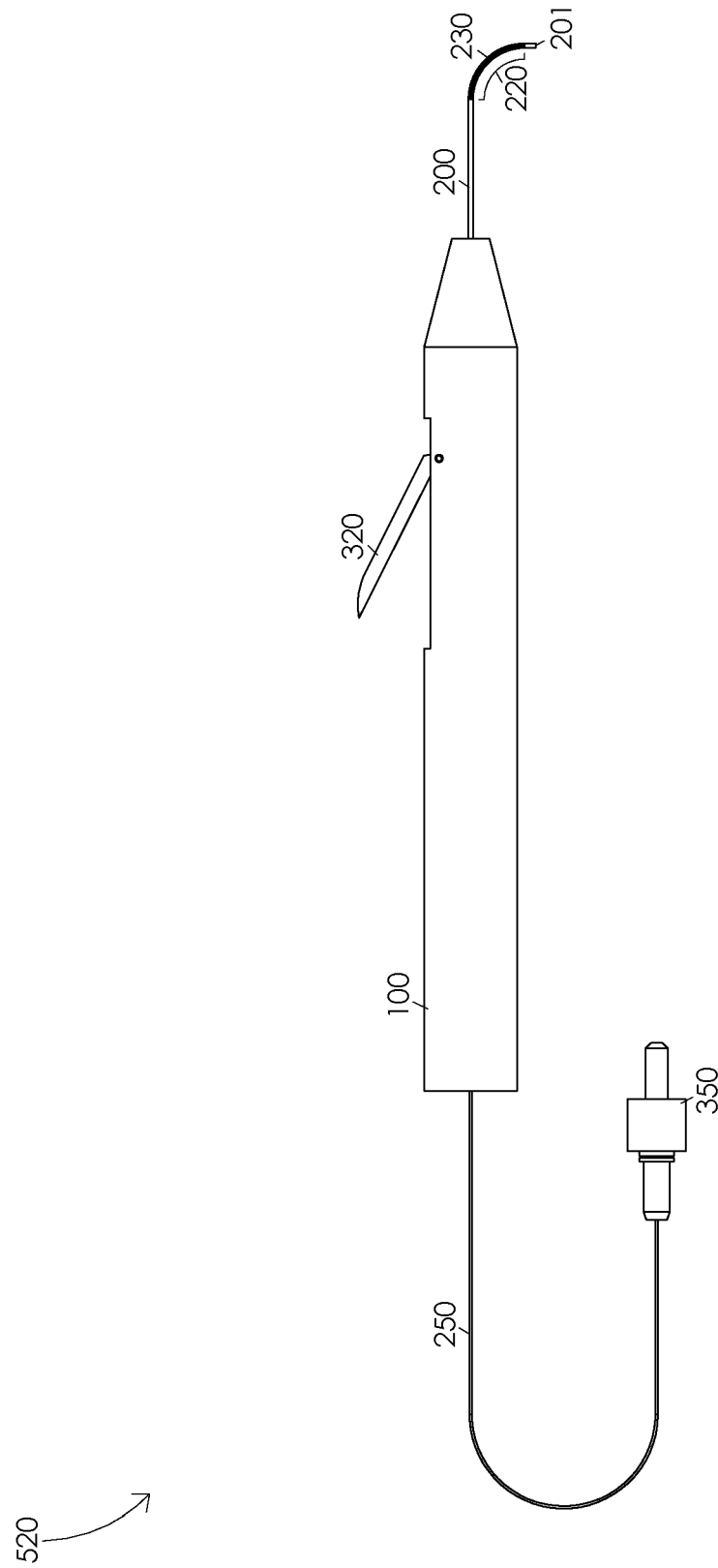

FIG. 5C illustrates an optic fiber in a second curved position 520. In one or more embodiments, a rotation of actuation lever 320 about pivot pin 310 in a counter-clockwise direction may be configured to gradually curve optic fiber 250 from an optic fiber in a first curved position 510 to an optic fiber in a second curved position 520. Illustratively, a rotation of actuation lever 320 about pivot pin 310 in a counter-clockwise direction may be configured to gradually extend piston 340 relative to handle proximal end 102. In one or more embodiments, a gradual extension of piston 340 relative to handle proximal end 102 may be configured to gradually extend housing tube 200 relative to cable 240. Illustratively, a gradual extension of housing tube 200 relative to cable 240 may be configured to cause cable 240 to apply a force, e.g., a compressive force, to a portion of housing tube 200. In one or more embodiments, an application of a force to a portion of housing tube 200 may be configured to compress a portion of housing tube 200, e.g., first housing tube portion 220. Illustratively, a compression of a portion of housing tube 200, e.g., first housing tube portion 220, may be configured to gradually curve housing tube 200. In one or more embodiments, a gradual curving of housing tube 200 may be configured to gradually curve optic fiber 250, e.g., from an optic fiber in a first curved position 510 to an optic fiber in a second curved position 520. Illustratively, a line tangent to optic fiber distal end 251 may intersect a line tangent to housing tube proximal end 202 at a second angle, e.g., when optic fiber 250 comprises an optic fiber in a second curved position 520. In one or more embodiments, the second angle may comprise any angle greater than the first angle. For example, the second angle may comprise a 90 degree angle.

Figure 5D:
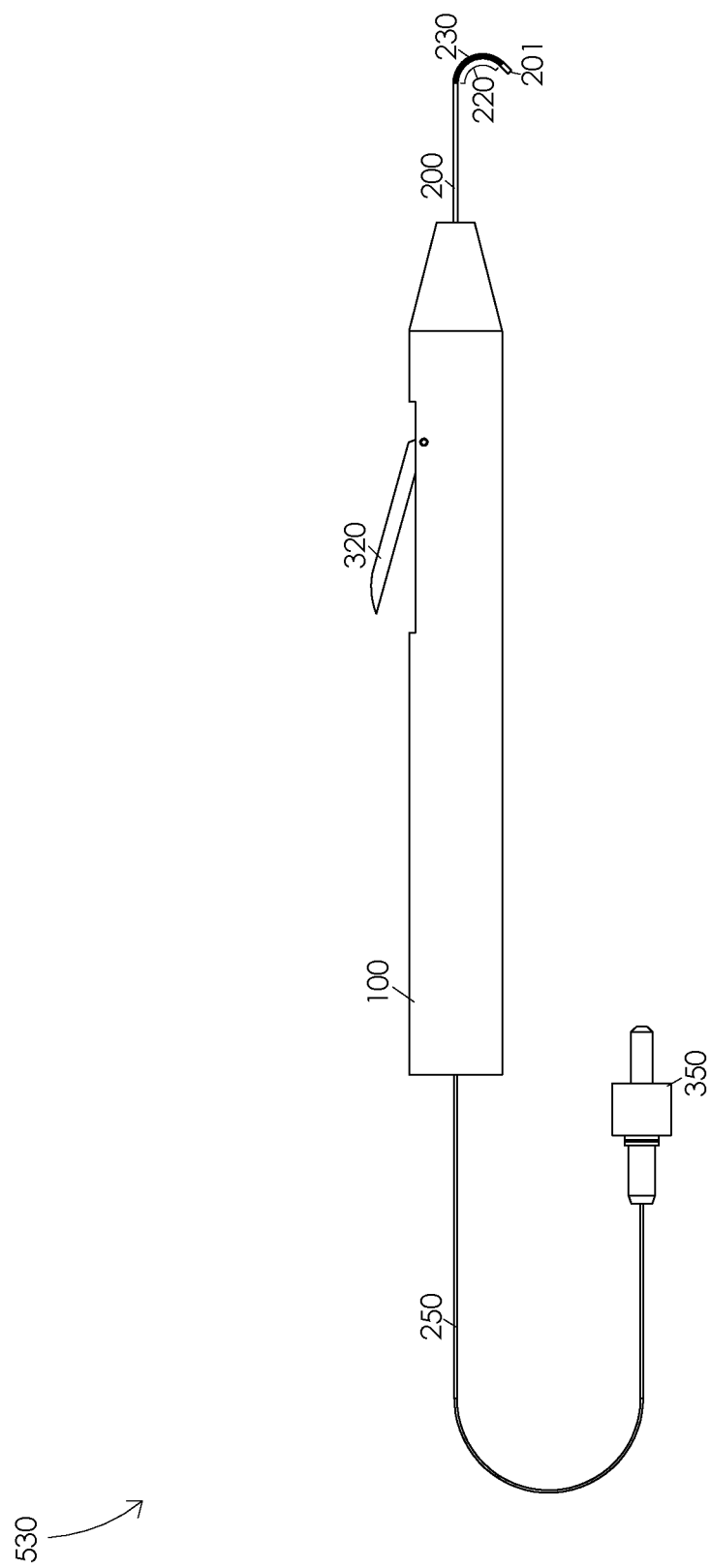

FIG. 5D illustrates an optic fiber in a third curved position 530. In one or more embodiments, a rotation of actuation lever 320 about pivot pin 310 in a counter-clockwise direction may be configured to gradually curve optic fiber 250 from an optic fiber in a second curved position 520 to an optic fiber in a third curved position 530. Illustratively, a rotation of actuation lever 320 about pivot pin 310 in a counter-clockwise direction may be configured to gradually extend piston 340 relative to handle proximal end 102. In one or more embodiments, a gradual extension of piston 340 relative to handle proximal end 102 may be configured to gradually extend housing tube 200 relative to cable 240. Illustratively, a gradual extension of housing tube 200 relative to cable 240 may be configured to cause cable 240 to apply a force, e.g., a compressive force, to a portion of housing tube 200. In one or more embodiments, an application of a force to a portion of housing tube 200 may be configured to compress a portion of housing tube 200, e.g., first housing tube portion 220. Illustratively, a compression of a portion of housing tube 200, e.g., first housing tube portion 220, may be configured to gradually curve housing tube 200. In one or more embodiments, a gradual curving of housing tube 200 may be configured to gradually curve optic fiber 250, e.g., from an optic fiber in a second curved position 520 to an optic fiber in a third curved position 530. Illustratively, a line tangent to optic fiber distal end 251 may intersect a line tangent to housing tube proximal end 202 at a third angle, e.g., when optic fiber 250 comprises an optic fiber in a third curved position 530. In one or more embodiments, the third angle may comprise any angle greater than the second angle. For example, the third angle may comprise a 135 degree angle.

Figure 5E:
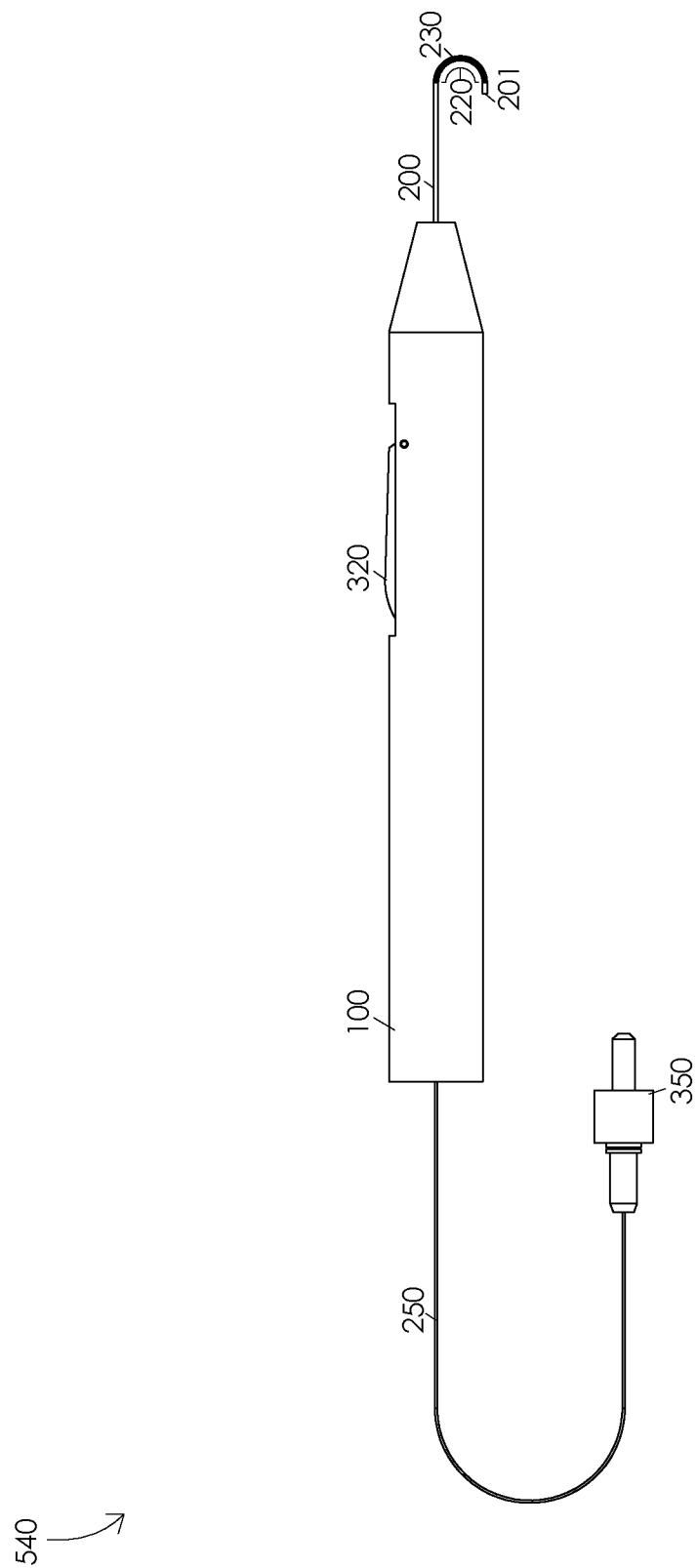

FIG. 5E illustrates an optic fiber in a fourth curved position 540. In one or more embodiments, a rotation of actuation lever 320 about pivot pin 310 in a counter-clockwise direction may be configured to gradually curve optic fiber 250 from an optic fiber in a third curved position 530 to an optic fiber in a fourth curved position 540. Illustratively, a rotation of actuation lever 320 about pivot pin 310 in a counter-clockwise direction may be configured to gradually extend piston 340 relative to handle proximal end 102. In one or more embodiments, a gradual extension of piston 340 relative to handle proximal end 102 may be configured to gradually extend housing tube 200 relative to cable 240. Illustratively, a gradual extension of housing tube 200 relative to cable 240 may be configured to cause cable 240 to apply a force, e.g., a compressive force, to a portion of housing tube 200. In one or more embodiments, an application of a force to a portion of housing tube 200 may be configured to compress a portion of housing tube 200, e.g., first housing tube portion 220. Illustratively, a compression of a portion of housing tube 200, e.g., first housing tube portion 220, may be configured to gradually curve housing tube 200. In one or more embodiments, a gradual curving of housing tube 200 may be configured to gradually curve optic fiber 250, e.g., from an optic fiber in a third curved position 530 to an optic fiber in a fourth curved position 540. Illustratively, a line tangent to optic fiber distal end 251 may be parallel to a line tangent to housing tube proximal end 202, e.g., when optic fiber 250 comprises an optic fiber in a fourth curved position 540.

In one or more embodiments, one or more properties of a steerable laser probe may be adjusted to attain one or more desired steerable laser probe features. For example, a length that housing tube distal end 201 extends from piston distal end 341 may be adjusted to vary a degree of rotation of actuation lever 320 configured to curve housing tube 200 to a particular curved position. Illustratively, a length of cable 240 may be adjusted to vary a degree of rotation of actuation lever 320 configured to curve housing tube 200 to a particular curved position. In one or more embodiments, a stiffness of first housing tube portion 220 or a stiffness of second housing tube portion 230 may be adjusted to vary a degree of rotation of actuation lever 320 configured to curve housing tube 200 to a particular curved position. Illustratively, a material comprising first housing tube portion 220 or a material comprising second housing tube portion 230 may be adjusted to vary a degree of rotation of actuation lever 320 configured to curve housing tube 200 to a particular curved position.

In one or more embodiments, a number of apertures in housing tube 200 may be adjusted to vary a degree of rotation of actuation lever 320 configured to curve housing tube 200 to a particular curved position. Illustratively, a location of one or more apertures in housing tube 200 may be adjusted to vary a degree of rotation of actuation lever 320 configured to curve housing tube 200 to a particular curved position. In one or more embodiments, a geometry of one or more apertures in housing tube 200 may be adjusted to vary a degree of rotation of actuation lever 320 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a position of pivot pin 310 may be adjusted to vary a degree of rotation of actuation lever 320 configured to curve housing tube 200 to a particular curved position. In one or more embodiments, a geometry of actuation lever 320 may be adjusted to vary a degree of rotation of actuation lever 320 configured to curve housing tube 200 to a particular curved position. Illustratively, one or more locations within housing tube 200 wherein cable 240 may be fixed to an inner portion of housing tube 200 may be adjusted to vary a degree of rotation of actuation lever 320 configured to curve housing tube 200 to a particular curved position. In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc.

Illustratively, an optic fiber sleeve may be configured to compress a portion of housing tube 200. For example, an optic fiber sleeve may enclose a portion of optic fiber 250 and the optic fiber sleeve may be fixed in a position relative to handle 100 and also fixed to a portion of housing tube 200. In one or more embodiments, a rotation of actuation lever 320 about pivot pin 310 in a counter-clockwise direction may be configured to extend housing tube 200 relative to an optic fiber sleeve. Illustratively, an extension of housing tube 200 relative to an optic fiber sleeve may be configured to cause the optic fiber sleeve to apply a force, e.g., a compressive force, to a portion of housing tube 200. In one or more embodiments, an application of a force to a portion of housing tube 200, e.g., first housing tube portion 220, may be configured to compress a portion of housing tube 200 causing housing tube 200 to gradually curve.

Illustratively, a pressure mechanism may be disposed within piston guide 160. In one or more embodiments, a pressure mechanism may be configured to provide a force. Illustratively, a pressure mechanism may comprise a spring or a coil configured to provide a force. In one or more embodiments, a pressure mechanism may be configured to provide a force to piston distal end 341. Illustratively, a pressure mechanism may provide a facilitating force configured to rotate actuation lever 320 in a clockwise direction about pivot pin 310. In one or more embodiments, a pressure mechanism may provide a resistive force configured to resist a rotation of actuation lever 320 in a counter-clockwise direction about pivot pin 310. Illustratively, a pressure mechanism may provide a force facilitating force configured to retract housing tube 200 relative to cable 240. In one or more embodiments, a pressure mechanism may provide a resistive force configured to resist an extension of housing tube 200 relative to cable 240.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

Figure 6A:
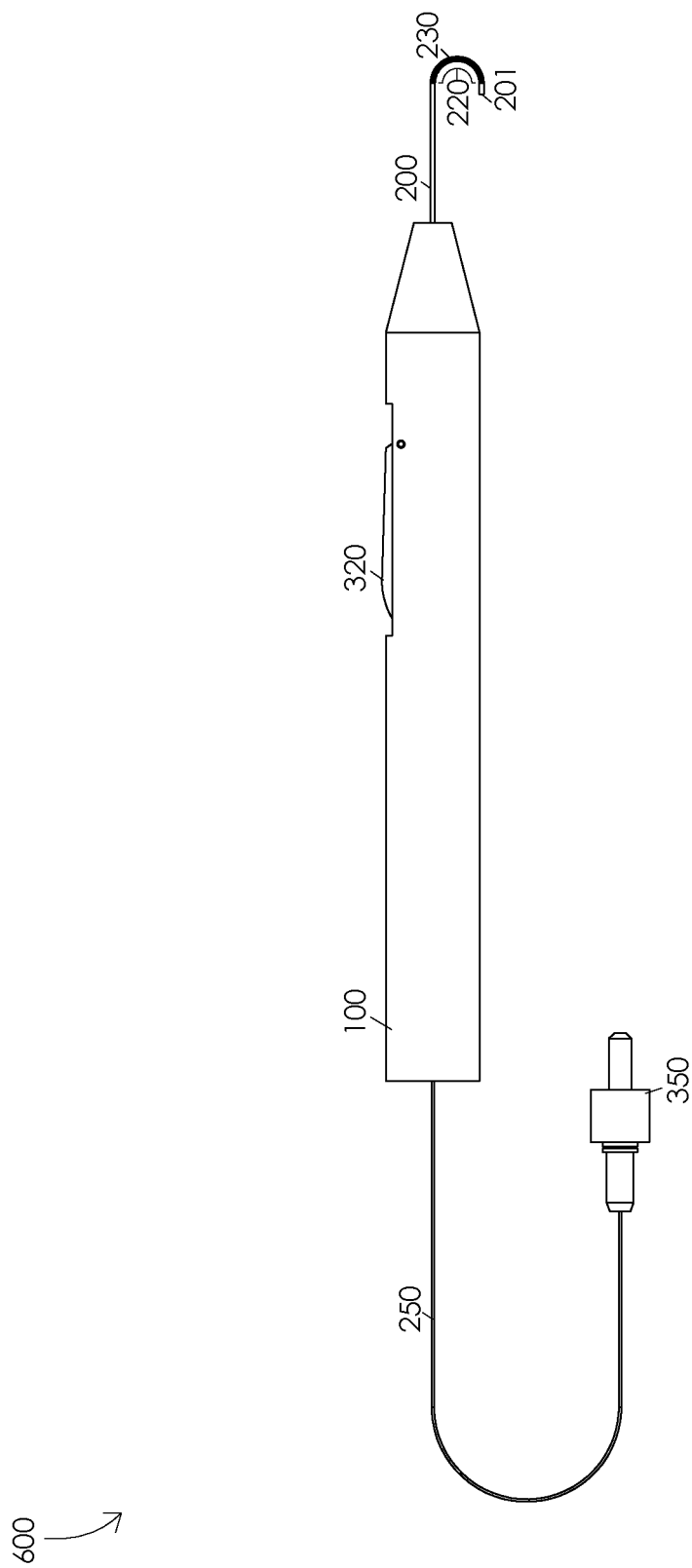
FIGS. 6A, 6B, 6C, 6D, and 6E are schematic diagrams illustrating a gradual straightening of an optic fiber.

FIGS. 6A, 6B, 6C, 6D, and 6E are schematic diagrams illustrating a gradual straightening of an optic fiber 250. FIG. 6A illustrates a fully curved optic fiber 600. In one or more embodiments, optic fiber 250 may comprise a fully curved optic fiber 600, e.g., when piston 340 is fully extended relative to handle proximal end 102. Illustratively, optic fiber 250 may comprise a fully curved optic fiber 600, e.g., when housing tube 200 is fully extended relative to cable 240. In one or more embodiments, optic fiber 250 may comprise a fully curved optic fiber 600, e.g., when first housing tube portion 220 is fully compressed. Illustratively, a line tangent to optic fiber distal end 251 may be parallel to a line tangent to housing tube proximal end 202, e.g., when optic fiber 250 comprises a fully curved optic fiber 600.

Figure 6B:
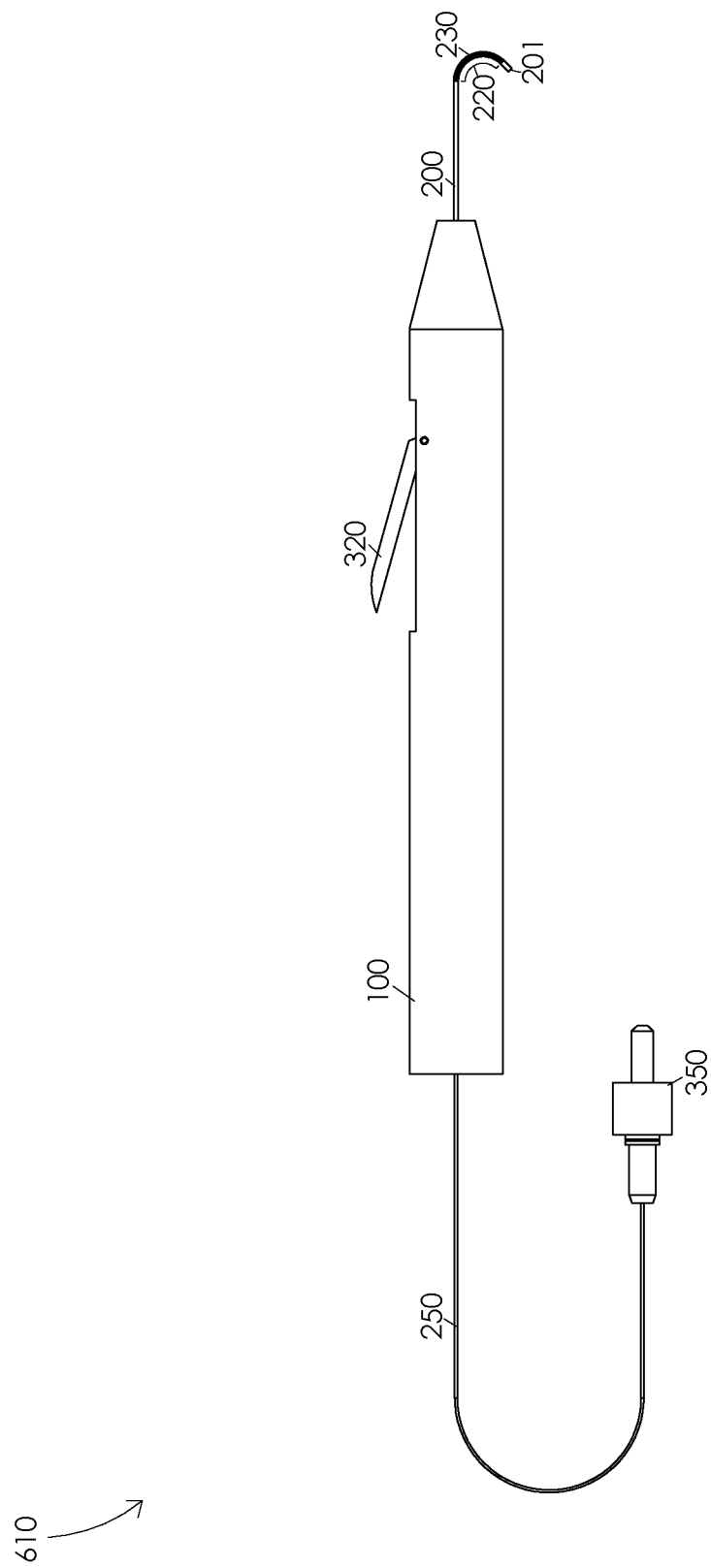

FIG. 6B illustrates an optic fiber in a first partially straightened position 610. In one or more embodiments, a rotation of actuation lever 320 about pivot pin 310 in a clockwise direction may be configured to gradually straighten optic fiber 250 from a fully curved optic fiber 600 to an optic fiber in a first partially straightened position 610. Illustratively, a rotation of actuation lever 320 about pivot pin 310 in a clockwise direction may be configured to gradually retract piston 340 relative to handle proximal end 102. In one or more embodiments, a gradual retraction of piston 340 relative to handle proximal end 102 may be configured to gradually retract housing tube 200 relative to cable 240. Illustratively, a retraction of housing tube 200 relative to cable 240 may be configured to reduce a force, e.g., a compressive force, applied to a portion of housing tube 200. In one or more embodiments, a reduction of a force applied to a portion of housing tube 200, e.g., first housing tube portion 220, may be configured to gradually decompress a portion of housing tube 200. Illustratively, a decompression of a portion of housing tube 200, e.g., first housing tube portion 220, may be configured to gradually straighten housing tube 200. In one or more embodiments, a gradual straightening of housing tube 200 may be configured to gradually straighten optic fiber 250, e.g., from a fully curved optic fiber 600 to an optic fiber in a first partially straightened position 610. Illustratively, a line tangent to optic fiber distal end 251 may intersect a line tangent to housing tube proximal end 202 at a first partially straightened angle, e.g., when optic fiber 250 comprises an optic fiber in a first partially straightened position 610. In one or more embodiments, the first partially straightened angle may comprise any angle less than 180 degrees. For example, the first partially straightened angle may comprise a 135 degree angle.

Figure 6C:
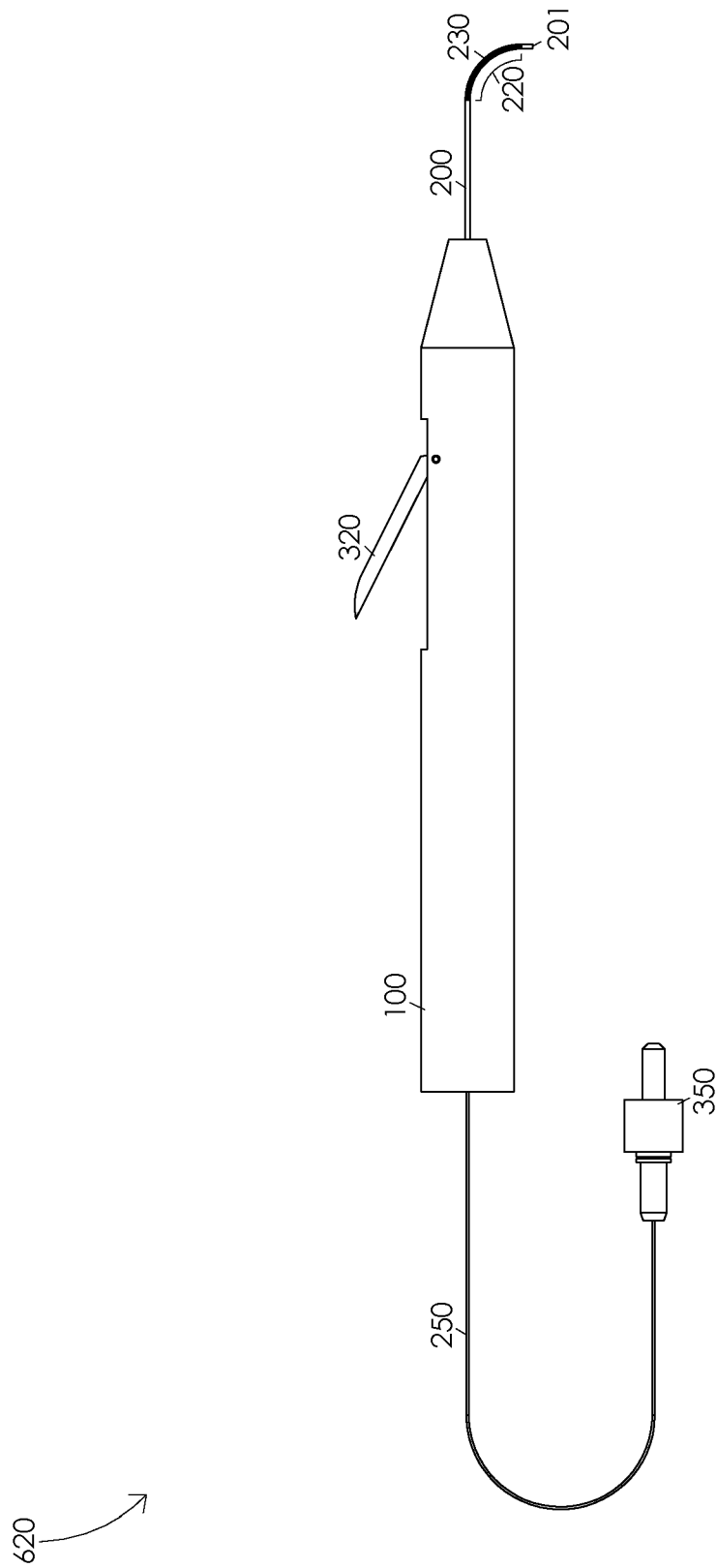

FIG. 6C illustrates an optic fiber in a second partially straightened position 620. In one or more embodiments, a rotation of actuation lever 320 about pivot pin 310 in a clockwise direction may be configured to gradually straighten optic fiber 250 from an optic fiber in a first partially straightened position 610 to an optic fiber in a second partially straightened position 620. Illustratively, a rotation of actuation lever 320 about pivot pin 310 in a clockwise direction may be configured to gradually retract piston 340 relative to handle proximal end 102. In one or more embodiments, a gradual retraction of piston 340 relative to handle proximal end 102 may be configured to gradually retract housing tube 200 relative to cable 240. Illustratively, a retraction of housing tube 200 relative to cable 240 may be configured to reduce a force, e.g., a compressive force, applied to a portion of housing tube 200. In one or more embodiments, a reduction of a force applied to a portion of housing tube 200, e.g., first housing tube portion 220, may be configured to gradually decompress a portion of housing tube 200. Illustratively, a decompression of a portion of housing tube 200, e.g., first housing tube portion 220, may be configured to gradually straighten housing tube 200. In one or more embodiments, a gradual straightening of housing tube 200 may be configured to gradually straighten optic fiber 250, e.g., from an optic fiber in a first partially straightened position 610 to an optic fiber in a second partially straightened position 620. Illustratively, a line tangent to optic fiber distal end 251 may intersect a line tangent to housing tube proximal end 202 at a second partially straightened angle, e.g., when optic fiber 250 comprises an optic fiber in a second partially straightened position 620. In one or more embodiments, the second partially straightened angle may comprise any angle less than the first partially straightened angle. For example, the second partially straightened angle may comprise a 90 degree angle.

Figure 6D:
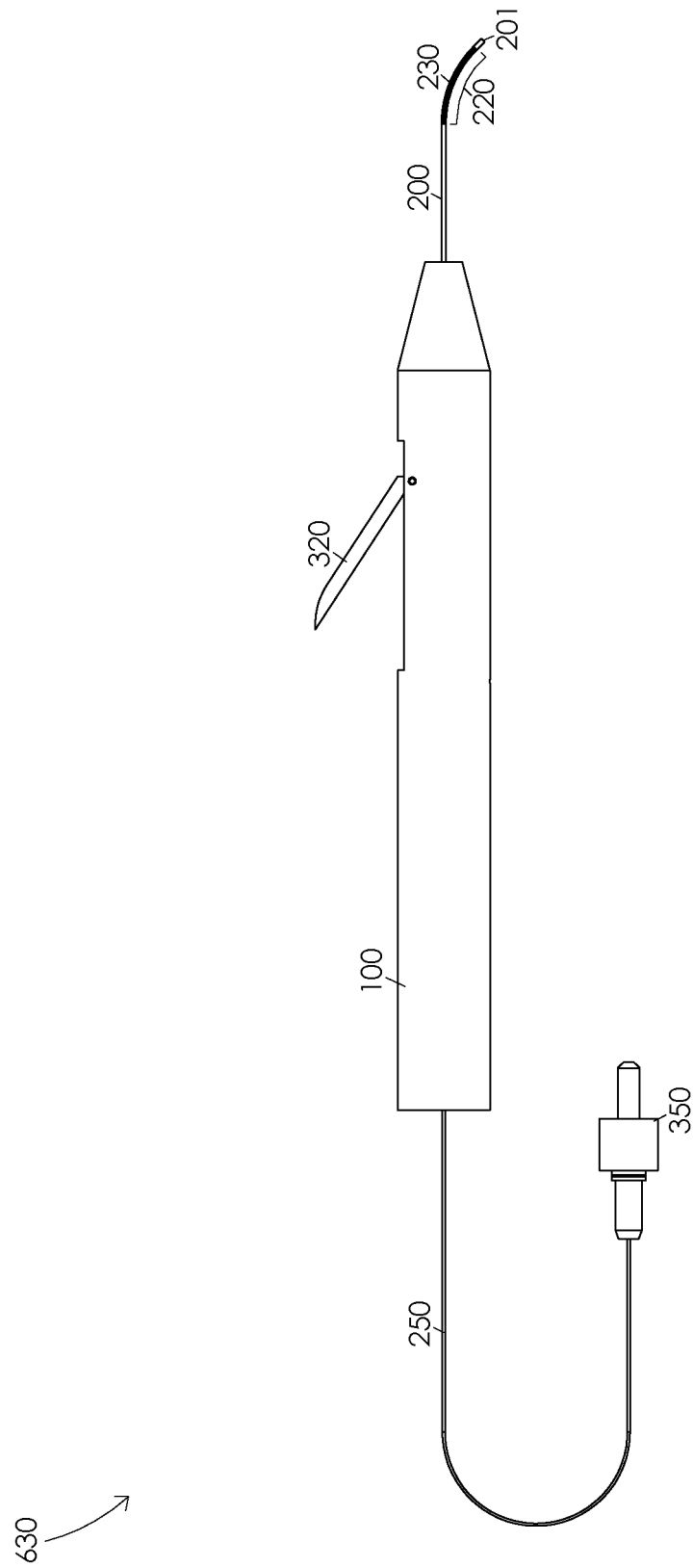

FIG. 6D illustrates an optic fiber in a third partially straightened position 630. In one or more embodiments, a rotation of actuation lever 320 about pivot pin 310 in a clockwise direction may be configured to gradually straighten optic fiber 250 from an optic fiber in a second partially straightened position 620 to an optic fiber in a third partially straightened position 630. Illustratively, a rotation of actuation lever 320 about pivot pin 310 in a clockwise direction may be configured to gradually retract piston 340 relative to handle proximal end 102. In one or more embodiments, a gradual retraction of piston 340 relative to handle proximal end 102 may be configured to gradually retract housing tube 200 relative to cable 240. Illustratively, a retraction of housing tube 200 relative to cable 240 may be configured to reduce a force, e.g., a compressive force, applied to a portion of housing tube 200. In one or more embodiments, a reduction of a force applied to a portion of housing tube 200, e.g., first housing tube portion 220, may be configured to gradually decompress a portion of housing tube 200. Illustratively, a decompression of a portion of housing tube 200, e.g., first housing tube portion 220, may be configured to gradually straighten housing tube 200. In one or more embodiments, a gradual straightening of housing tube 200 may be configured to gradually straighten optic fiber 250, e.g., from an optic fiber in a second partially straightened position 620 to an optic fiber in a third partially straightened position 630. Illustratively, a line tangent to optic fiber distal end 251 may intersect a line tangent to housing tube proximal end 202 at a third partially straightened angle, e.g., when optic fiber 250 comprises an optic fiber in a third partially straightened position 630. In one or more embodiments, the third partially straightened angle may comprise any angle less than the second partially straightened angle. For example, the third partially straightened angle may comprise a 45 degree angle.

Figure 6E:
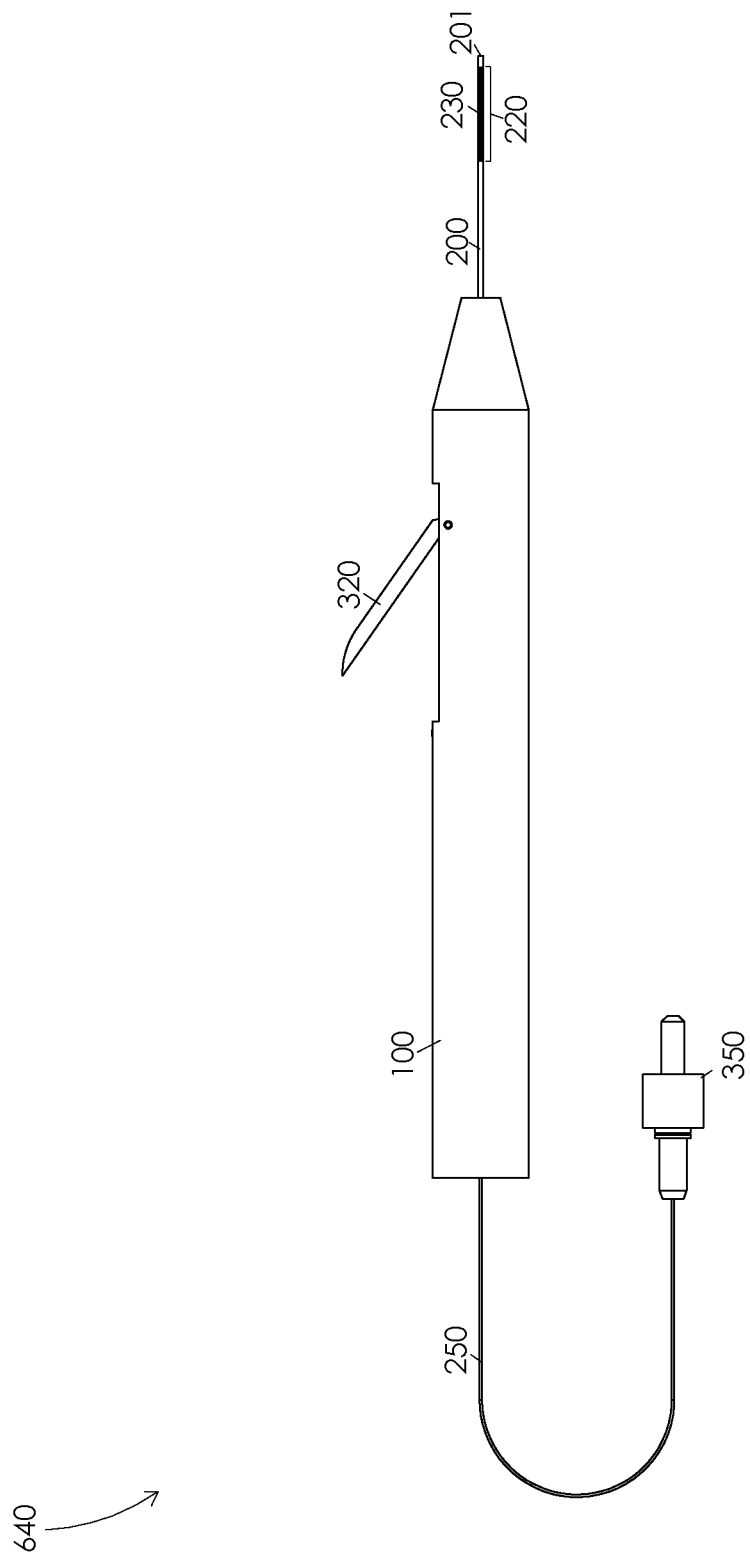

FIG. 6E illustrates an optic fiber in a fully straightened position 640. In one or more embodiments, a rotation of actuation lever 320 about pivot pin 310 in a clockwise direction may be configured to gradually straighten optic fiber 250 from an optic fiber in a third partially straightened position 630 to an optic fiber in a fully straightened position 640. Illustratively, a rotation of actuation lever 320 about pivot pin 310 in a clockwise direction may be configured to gradually retract piston 340 relative to handle proximal end 102. In one or more embodiments, a gradual retraction of piston 340 relative to handle proximal end 102 may be configured to gradually retract housing tube 200 relative to cable 240. Illustratively, a retraction of housing tube 200 relative to cable 240 may be configured to reduce a force, e.g., a compressive force, applied to a portion of housing tube 200. In one or more embodiments, a reduction of a force applied to a portion of housing tube 200, e.g., first housing tube portion 220, may be configured to gradually decompress a portion of housing tube 200. Illustratively, a decompression of a portion of housing tube 200, e.g., first housing tube portion 220, may be configured to gradually straighten housing tube 200. In one or more embodiments, a gradual straightening of housing tube 200 may be configured to gradually straighten optic fiber 250, e.g., from an optic fiber in a third partially straightened position 630 to an optic fiber in a fully straightened position 640. Illustratively, a line tangent to optic fiber distal end 251 may be parallel to a line tangent to housing tube proximal end 202, e.g., when optic fiber 250 comprises an optic fiber in a fully straightened position 640.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient housing tube 200 in an orientation configured to cause a curvature of housing tube 200 within the particular transverse plane of the inner eye and varying a degree of rotation of actuation lever 320 about pivot pin 310. Illustratively, a surgeon may aim optic fiber distal end 251 at any target within a particular sagittal plane of the inner eye by, e.g., rotating handle 100 to orient housing tube 200 in an orientation configured to cause a curvature of housing tube 200 within the particular sagittal plane of the inner eye and varying a degree of rotation of actuation lever 320 about pivot pin 310. In one or more embodiments, a surgeon may aim optic fiber distal end 251 at any target within a particular frontal plane of the inner eye by, e.g., varying a degree of rotation of actuation lever 320 about pivot pin 310 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying a degree of rotation of actuation lever 320 about pivot pin 310. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. An instrument comprising:
   a handle having a handle distal end and a handle proximal end;
   an inner bore of the handle;
   a piston guide of the handle;
   an actuation lever guide of the handle, the actuation lever guide disposed between the inner bore and the piston guide;
   a single piston having a piston distal end and a piston proximal end, the piston disposed within the piston guide of the inner bore of the handle wherein the piston distal end is disposed between the handle distal end and the handle proximal end and the piston proximal end is disposed between the handle distal end and the handle proximal end;
   a housing tube having a housing tube distal end and a housing tube proximal end, the housing tube disposed within the piston and a housing tube guide of the handle wherein the housing tube proximal end is fixed within an inner bore of the piston and the housing tube distal end extends from the handle distal end;
   an optic fiber having an optic fiber distal end and an optic fiber proximal end, the optic fiber disposed within the inner bore of the handle and the housing tube wherein the optic fiber distal end is adjacent to the housing tube distal end;
   a single actuation lever having an actuation lever distal end, an actuation lever proximal end, and a pivot pin chamber, the actuation lever fixed to the handle by a pivot pin disposed within the pivot pin chamber wherein the actuation lever proximal end is disposed in the actuation lever guide and wherein the actuation lever distal end is not disposed in the actuation lever guide, the actuation lever configured to actuate about the pivot pin and actuate the piston relative to the handle proximal end wherein the actuation lever is configured to actuate about the pivot pin in a first direction and in a second direction and wherein the piston is disposed between the handle distal end and the actuation lever; and a cable having a cable distal end and a cable proximal end, the cable disposed within the housing tube and within the handle wherein a first portion of the cable is fixed to the housing tube and a second portion of the cable is fixed in a position relative to the handle.

2. The instrument of claim 1 wherein an actuation of the actuation lever about the pivot pin in the first direction is configured to curve the optic fiber.

3. The instrument of claim 2 wherein the actuation of the actuation lever about the pivot pin in the first direction is configured to curve the optic fiber within an eye without increasing a length of the instrument within the eye.

4. The instrument of claim 2 wherein the actuation of the actuation lever about the pivot pin in the first direction is configured to curve the optic fiber within an eye without decreasing a length of the instrument within the eye.

5. The instrument of claim 1 wherein an actuation of the actuation lever about the pivot pin in the second direction is configured to straighten the optic fiber.

6. The instrument of claim 5 wherein the actuation of the actuation lever about the pivot pin in the second direction is configured to straighten the optic fiber within an eye without increasing a length of the instrument within the eye.

7. The instrument of claim 5 wherein the actuation of the actuation lever about the pivot pin in the second direction is configured to straighten the optic fiber within an eye without decreasing a length of the instrument within the eye.

8. The instrument of claim 1 wherein an actuation of the actuation lever about the pivot pin in the first direction is configured to extend the piston relative to the handle proximal end.

9. The instrument of claim 1 wherein an actuation of the actuation lever about the pivot pin in the second direction is configured to retract the piston relative to the handle proximal end.

10. The instrument of claim 1 wherein an actuation of the actuation lever about the pivot pin in the first direction is configured to extend the housing tube relative to the handle proximal end.

11. The instrument of claim 10 wherein the actuation of the actuation lever about the pivot pin in the first direction is configured to extend the housing tube relative to the cable.

12. The instrument of claim 1 wherein an actuation of the actuation lever about the pivot pin in the second direction is configured to retract the housing tube relative to the handle proximal end.

13. The instrument of claim 12 wherein the actuation of the actuation lever about the pivot pin in the second direction is configured to retract the housing tube relative to the cable.

14. An instrument comprising:
a handle having a handle distal end and a handle proximal end;
an inner bore of the handle;
a piston guide of the handle;
an actuation lever guide of the handle, the actuation lever guide disposed between the inner bore and the piston guide;
a single piston having a piston distal end and a piston proximal end, the piston disposed within the piston guide of the inner bore of the handle wherein the piston distal end is disposed between the handle distal end and the handle proximal end and the piston proximal end is disposed between the handle distal end and the handle proximal end;

a housing tube having a housing tube distal end and a housing tube proximal end, the housing tube disposed within the piston and a housing tube guide of the handle wherein the housing tube proximal end is fixed within an inner bore of the piston and the housing tube distal end extends from the handle distal end;

an optic fiber having an optic fiber distal end and an optic fiber proximal end, the optic fiber disposed within the inner bore of the handle and the housing tube wherein the optic fiber distal end is adjacent to the housing tube distal end;

a single actuation lever having an actuation lever distal end, an actuation lever proximal end, and a pivot pin chamber, the actuation lever fixed to the handle by a pivot pin disposed within the pivot pin chamber wherein the actuation lever proximal end is disposed in the actuation lever guide and wherein the actuation lever distal end is not disposed in the actuation lever guide, the actuation lever configured to actuate about the pivot pin and actuate the piston relative to the handle proximal end wherein the actuation lever is configured to actuate about the pivot pin in a first direction and in a second direction and wherein the piston is disposed between the handle distal end and the actuation lever; and a cable having a cable distal end and a cable proximal end, the cable disposed within the housing tube and within the handle wherein a first portion of the cable is fixed to the housing tube and a second portion of the cable is fixed in a position relative to the handle and wherein an actuation of the actuation lever about the pivot pin in the first direction is configured to extend the housing tube relative to the cable.

15. The instrument of claim 14 wherein the actuation of the actuation lever about the pivot pin in the first direction is configured to curve the optic fiber.

16. The instrument of claim 14 wherein the actuation of the actuation lever about the pivot pin in the first direction is configured to curve the optic fiber within an eye without increasing a length of the instrument within the eye.

17. The instrument of claim 14 wherein the actuation of the actuation lever about the pivot pin in the first direction is configured to curve the optic fiber within an eye without decreasing a length of the instrument within the eye.

18. An instrument comprising:
a handle having a handle distal end and a handle proximal end;
an inner bore of the handle;
a piston guide of the handle;
an actuation lever guide of the handle, the actuation lever guide disposed between the inner bore and the piston guide;
a single piston having a piston distal end and a piston proximal end, the piston disposed within the piston guide of the inner bore of the handle wherein the piston distal end is disposed between the handle distal end and the handle proximal end and the piston proximal end is disposed between the handle distal end and the handle proximal end;
a housing tube having a housing tube distal end and a housing tube proximal end, the housing tube disposed within the piston and a housing tube guide of the handle wherein the housing tube proximal end is fixed within an inner bore of the piston and the housing tube distal end extends from the handle distal end;

an optic fiber having an optic fiber distal end and an optic fiber proximal end, the optic fiber disposed within the inner bore of the handle and the housing tube wherein the optic fiber distal end is adjacent to the housing tube distal end;

a single actuation lever having an actuation lever distal end, an actuation lever proximal end, and a pivot pin chamber, the actuation lever fixed to the handle by a pivot pin disposed within the pivot pin chamber wherein the actuation lever proximal end is disposed in the actuation lever guide and wherein the actuation lever distal end is not disposed in the actuation lever guide, the actuation lever configured to actuate about the pivot pin and actuate the piston relative to the handle proximal end wherein the actuation lever is configured to actuate about the pivot pin in a first direction and in a second direction and wherein the piston is disposed between the handle distal end and the actuation lever; and a cable having a cable distal end and a cable proximal end, the cable disposed within the housing tube and within the handle wherein a first portion of the cable is fixed to the housing tube and a second portion of the cable is fixed in a position relative to the handle and wherein an actuation of the actuation lever about the pivot pin in the second direction is configured to retract the housing tube relative to the cable.

19. The instrument of claim 18 wherein the actuation of the actuation lever about the pivot pin in the second direction is configured to straighten the optic fiber.

20. The instrument of claim 19 wherein the actuation of the actuation lever about the pivot pin in the second direction is configured to straighten the housing tube.

* * * * *